US009968749B2

(12) United States Patent
Hansmann et al.

(10) Patent No.: US 9,968,749 B2
(45) Date of Patent: May 15, 2018

(54) RESPIRATION SYSTEM

(71) Applicant: Dräger Medical GmbH, Lübeck (DE)

(72) Inventors: Hans-Ullrich Hansmann, Barnitz (DE); Marcus Eger, Lübeck (DE); Peter Bach, Lübeck (DE); Leenderd Van Eykern, Zuidhorn (NL)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 813 days.

(21) Appl. No.: 13/772,687

(22) Filed: Feb. 21, 2013

(65) Prior Publication Data

US 2013/0213399 A1   Aug. 22, 2013

(30) Foreign Application Priority Data

Feb. 22, 2012   (DE) .................. 10 2012 003 509

(51) Int. Cl.
*A61M 16/00* (2006.01)
*A61B 5/0488* (2006.01)
(Continued)

(52) U.S. Cl.
CPC ......... *A61M 16/00* (2013.01); *A61B 5/02405* (2013.01); *A61B 5/0402* (2013.01);
(Continued)

(58) Field of Classification Search
CPC ............. A61M 16/00; A61M 16/0051; A61M 2230/60; A61M 2205/8206;
(Continued)

(56) References Cited

U.S. PATENT DOCUMENTS 5,671,752 A  *  9/1997  Sinderby ............ A61B 5/04884
                                                          600/546
5,820,560 A  *  10/1998 Sinderby et al. ............. 600/546
(Continued)

FOREIGN PATENT DOCUMENTS

CN          1 713 850 A    12/2005
CN        101 203 260 A     6/2008
(Continued)

OTHER PUBLICATIONS

Article in Conference proceedings: Denoising of Diaphragmatic Electromyogram Signals for Respiratory Control and Diagnostic Purposes Annual International Conference of the IEEE Engineering in Medicine and Biology Society. IEEE Engineering in Medicine and Biology Society. Conference • Feb. 2008.*

(Continued)

*Primary Examiner* — Todd J Scherbel
*Assistant Examiner* — Ned T Heffner
(74) *Attorney, Agent, or Firm* — McGlew and Tuttle, P.C.

(57) ABSTRACT

A respiration system for noninvasive respiration includes a respiration drive, which is controlled by a control device, and includes a patient module (4) with electrodes for picking up electrode signals from the surface of the chest of a patient. The control device is set up to suppress ECG signals in the electrode signals in order to obtain electromyographic signals (EMG signals) representing the breathing effort and to control the respiration drive as a function of the EMG signals. Provisions are made for deriving ECG signals from the electrode signals before said ECG signals are suppressed and for making data representative of the ECG available for display.

16 Claims, 5 Drawing Sheets

(51) Int. Cl.
*A61B 5/00* (2006.01)
*A61B 5/024* (2006.01)
*A61B 5/0402* (2006.01)

(52) U.S. Cl.
CPC .......... *A61B 5/0488* (2013.01); *A61B 5/7203* (2013.01); *A61M 16/0051* (2013.01); *A61M 2205/502* (2013.01); *A61M 2205/8206* (2013.01); *A61M 2230/04* (2013.01); *A61M 2230/60* (2013.01)

(58) Field of Classification Search
CPC ........ A61M 2205/502; A61M 2230/04; A61B 5/7203; A61B 5/0402; A61B 5/02405; A61B 5/0488
USPC ............ 128/204.23, 204.21, 200.14, 203.12, 128/203.13
See application file for complete search history.

(56) References Cited

U.S. PATENT DOCUMENTS

| | | | | |
|---|---|---|---|---|
| 6,411,843 | B1* | 6/2002 | Zarychta | ................. 600/546 |
| 8,109,269 | B2* | 2/2012 | Eger | ............... A61B 5/0488 128/200.14 |
| 2005/0126578 | A1* | 6/2005 | Garrison | .............. A61H 9/0078 128/874 |
| 2007/0191728 | A1 | 8/2007 | Shennib | |
| 2007/0276270 | A1* | 11/2007 | Tran | ........................ 600/508 |
| 2008/0000479 | A1* | 1/2008 | Elaz | ...................... A61B 5/412 128/204.23 |
| 2008/0190430 | A1* | 8/2008 | Melker et al. | ............ 128/204.23 |
| 2008/0308104 | A1* | 12/2008 | Blomberg et al. | ....... 128/204.23 |
| 2009/0159082 | A1 | 6/2009 | Eger | |
| 2010/0180896 | A1* | 7/2010 | Blomquist | ......... A61B 5/04884 128/204.23 |
| 2010/0234718 | A1* | 9/2010 | Sampath et al. | ............. 600/407 |
| 2011/0028819 | A1* | 2/2011 | Eger et al. | .................... 600/372 |
| 2011/0240021 | A1 | 10/2011 | Eger et al. | |

FOREIGN PATENT DOCUMENTS

| | | |
|---|---|---|
| DE | 10 2007 062 214 B3 | 8/2009 |
| DE | 10 2009 035 018 A1 | 2/2011 |
| EP | 2 371 412 A1 | 10/2011 |
| WO | 2005/096924 A1 | 10/2005 |

OTHER PUBLICATIONS

French Search Report dated Mar. 18, 2016.

* cited by examiner

RESPIRATION SYSTEM

CROSS REFERENCE TO RELATED APPLICATIONS

This application claims the benefit of priority under 35 U.S.C. § 119 of German Patent Application 10 2012 003 509.8 filed Feb. 22, 2012, the entire contents of which are incorporated herein by reference.

FIELD OF THE INVENTION

The present invention pertains to a respiration system (also known as a ventilation system) for noninvasive respiration (also known as ventilation) with a respiration drive (ventilator drive), which is controlled by a control means, and with electrodes for picking up electrode signals from the surface of the chest, wherein the control means is set up to suppress electrocardiogram (ECG, also known as EKG) components in the electrode signal in order to obtain electromyographic signals (EMG signals) representing the breathing effort and to control the respiration drive as a function of the EMG signals, wherein the control means derives ECG signals from the electrode signal and makes the signals available for display before suppression of the ECG signal component.

BACKGROUND OF THE INVENTION

The goal of respiration systems is to relieve the respiratory muscles of the patient and to guarantee sufficient oxygen supply and carbon dioxide elimination. This happens either by the breathing work being assumed by a breathing drive either completely or partly in case of assisted methods. In view of the increase in chronic lung diseases and the need for improved therapy, noninvasive breathing support in case of improved interaction between patient and respiration drive is an important requirement for modern respiration systems. An essential aspect is the setting of the percentage that the device contributes to the breathing work relative to the percentage contributed to the breathing work by the patient himself/herself (corresponding to the amplitudes of the breaths) and the synchronicity in time. Various goals, e.g., relieving the patient's muscles or weaning from a respirator, can be pursued with an adjustable percentage of spontaneous breathing. It is important for this to detect the beginning of the phases of the patient's breathing with certainty, because this information does not unambiguously appear from the measured pneumatic signals of the respiration system, especially in neonates and COPD patients. It is known that electromyographic signals (EMG signals), which represent the activity of the breathing muscles, can be picked up to improve the adaptation to the patient's breathing efforts. Such a method is known from DE 10 2007 062 214 B3 (corresponding to U.S. Pat. No. 8,109,269). A breathing activity signal $u_{EMG}(t)$ is picked up with electrodes on the surface of the chest with the prior-art device. To make the electrode signals picked up into electromyographic signals representing the breathing activity, the electrode signals must be subjected to preprocessing; in particular, ECG signal components, which dominate the entire signal in terms of signal level, must be removed. Filtering as well as envelope detection may be performed for this. The envelope detection is preferably performed by absolute value determination or squaring and subsequent low pass filtering of the electrode signals. Electromyographic signals, which can be used to control the respiration drive of the respiration system, as is described, e.g., in DE 10 2007 062 214 B3, are obtained after this preprocessing.

It is also desirable during the respiration of patients to display an electrocardiogram (ECG) in order to have an overview of the vital parameters. This display shall be used to make visible the heart rate as well as the uniformity (variability) and irregularities (arrhythmia) in the display.

A plurality of electrodes are necessary for recording the electromyographic signals on the surface of the chest. If there are no cardiological issues, an ECG is usually recorded with three leads, i.e., four electrodes in the patient's chest region. If an ECG signal shall also be recorded besides an electromyographic signal, many electrodes must therefore be attached to the patient's upper body, which is disadvantageous especially for very small patients and premature babies.

Provisions are made according to DE 10 2009 035 018 A1 (corresponding to US 2011028819 A1), for the control device to be set up to pick up ECG signals from the electrode signals recorded before the ECG signal components are suppressed and to make data representative of the ECG available for display.

The electromyographic surface electrode signals, just as the signals of an esophageal EMG, do indeed contain a large signal component due to the cardiac activity (ECG signals). This signal component, with a signal amplitude of one to several mV, is eliminated from the signal curve in order to make it possible to rate the substantially lower other muscle activities (for example, diaphragmatic, intercostal and accessory respiratory muscles) as breathing activity signals. The ECG component is processed for this by subtracting or cutting out the ECG signals; as a rule, the signal components that contain an R peak of the ECG signal and cut out in a fixed time window before and after the R peak. The cut-out signal components are replaced either by 0 or a constant corresponding to the signal level before the time window of the R peak of the ECG signal, i.e., the signal is extrapolated over the time window with the signal level before the time window of the R peak. The eliminated ECG component of the electrode signals is not in a direct relationship with the patient's breathing efforts and is unremarkable in case of controlling breathing on the basis of the EMG signals. The EMG signals obtained after suppression of the ECG signal components are signals whose amplitude is modulated with the muscle activity.

The ECG signals present before they are suppressed can be picked up as ECG signals and displayed on a display. Leads, which approximately correspond to the usual leads of an ECG according to Einthoven I or II, are formed when the electrodes are positioned for detecting the EMG component. It is necessary for a diagnostic ECG to know the positions and hence the angles of view to the heart as a voltage generator (Cabrera circle) in order for the graphic representation to correspond to the modes of representation common in medicine and for the amplitude and time ratios to be able to be measured corresponding to the medical standards.

The electrodes are arranged at a patient module, which is to be placed on the surface of the patient's chest.

SUMMARY OF THE INVENTION

An object of the present invention is to improve a respiration system such that more information, especially on the status of the cardiocirculatory system, is available to the users.

According to the invention, a respiration system is provided for noninvasive respiration. The respiration system comprises a respiration drive a patient module with electrodes for picking up electrode signals from the surface of the chest of a patient and a control device controlling the respiration drive. The control device is configured to receive electrode signals from the patient module, suppress electrocardiogram (ECG) components in the electrode signals in order to obtain electromyographic signals (EMG signals) representing the breathing effort and control the respiration drive as a function of the EMG signals. The control device picks up ECG signals from the electrode signals before the ECG signal component is suppressed and making data representative of the ECG available for display. The control device is further configured to form an envelope for the EMG signals after separation of the ECG signals and to display it on the respirator, to determine a heart rate as a measured value from the ECG signal and to display the heart rate together with the ECG signal on the respirator or to make the heart rate together with the ECG signal available at the outputs for display on a separate monitor.

Provisions are made according to the present invention for the control means to be set up, furthermore, to form an envelope for the EMG signals after separation of the ECG signals and to display it on the respirator, to determine the heart rate as a measured value from the ECG signal and to display the heart rate together with the ECG signal on the respirator or to make these available at the outputs for display on a separate monitor.

The control means, individual components of which may already be accommodated on the patient module or at another location in the respiration system, makes the separated ECG signals available in the digital and/or analog form in order to make possible the graphic representation together with the display of the heart rate as measured values on a patient monitor.

The heart rate and optionally the heart rate variability are determined and displayed as measured values.

The heart rate variability can be determined over a settable time period (for example, 1,000 to 10,000 heart beats) and displayed as a standard deviation, as a histogram or as a frequency spectrum. The heart rate variability can be used to assess the load of the cardiovascular system or to generate a stress index therefrom. The adaptation to the breathing cycle can also be derived from the variability of the heart rate. The physiological breathing and cardiac activities are controlled in the first order independently from one another according to the need for gas exchange ($CO_2$ as a command variable) and the need for nutrient/oxygen transport in the tissue. In the second order, the physiological breathing and cardiac activities are coupled by the body attempting to facilitate a superposition of low breathing pressures (inspiration) and the filling of the atrium with venous, pressureless blood. Coupling of breathing and cardiac activity can therefore be observed under healthy physiological conditions. Both control loops (circuits) have a degree of freedom over a frequency range and an excursion range. Whether other, "less important" influential factors can affect the cardiac activity or whether the heart is working at the limit of its performance capacity and cannot take any "unimportant" influencing variables into account can be derived from the variability.

The respiration system may have in a monitor a separate area, in which graphic display of the ECG signals picked up and/or measured values derived therefrom are displayed. The monitor may be mechanically directly integrated with the respiration system or positioned as a separate part at a spaced location therefrom.

The present invention will be explained below on the basis of exemplary embodiments shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
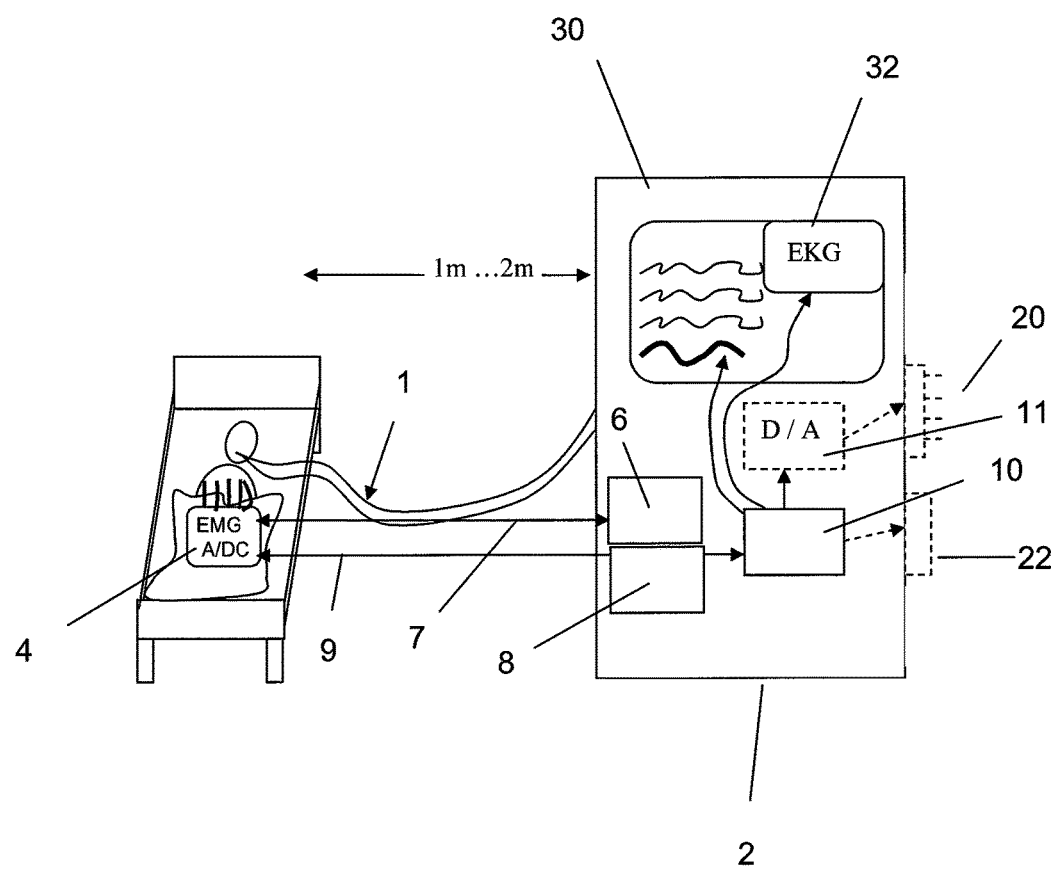
FIG. 1 is a schematic view of a respiration system according to the invention.

Referring to the drawings in particular, FIG. 1 shows a respiration system with a main unit 2 and with a patient module 4, which is provided with electrodes, which are placed on the surface of the patient's chest. The patient module 4 is in connection with the main unit 2 by means of a line 9, which is connected with a circuit 8 for potential separation for energy supply, and by means of a line 7 for data transmission. The noninvasive respiration takes place via a tube system 1 with an inspiratory tube and an expiratory tube.

The signals picked up by the electrodes are converted into digital data by analog/digital converters that are part of the patient module 4, and these data are transmitted to the main unit 2 via a line 7. The digital data transmitted over the line 7 are converted in a DC-DC converter circuit 6 and transmitted further to a control device (control means) 10, e.g., in the form of a microprocessor, in which, among other things, ECG (EKG) signals are separated. ECG signals are sent, on the one hand, to a digital ECG output 22 in digital form; on the other hand, ECG signals are converted again into an analog signal in a digital/analog converter 11, and this analog signal is sent to an analog ECG output 20. The main unit 2 has a display 30, on which the electromyographic signals are displayed after separation of the ECG signal component. The heart rate obtained from the ECG signals is additionally displayed on display 30 as a measured value together with the ECG signals. The electromyographic signals are used in the control device 10 to set the support of breathing activity by a respiration drive according to preset algorithms, e.g., as described in DE 10 2007 062 214 B3 (corresponding to U.S. 8,109,269 which is incorporated herein by reference).

The signals picked up by the electrodes may, of course, also be transmitted in the analog form from the patient module to the main unit via a line and digitized in the main unit only in an exemplary embodiment, which is not shown.

Figure 2:
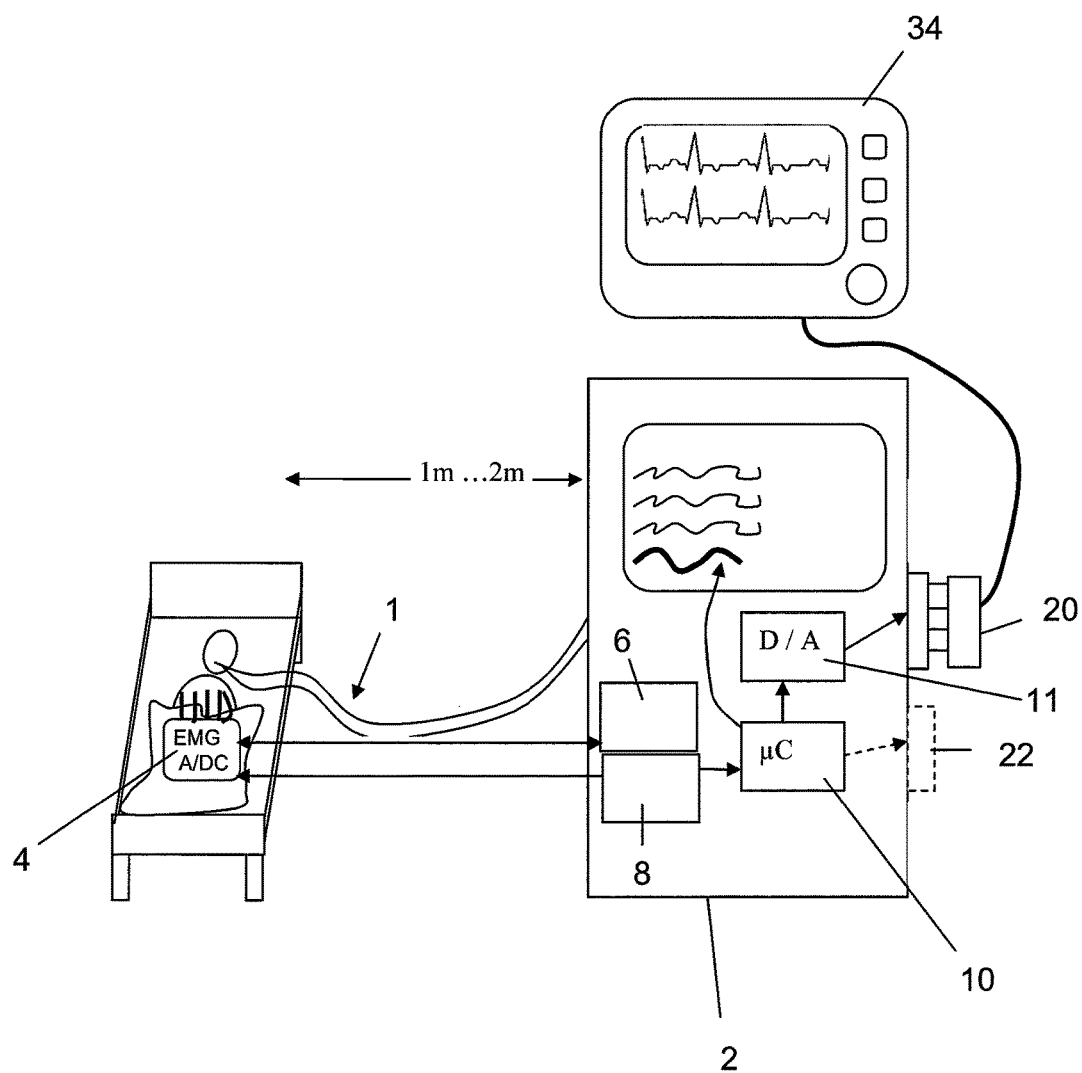
FIG. 2 is a schematic view of a respiration system according to the invention.

FIG. 2 shows another embodiment of a respiration system, which largely corresponds to that shown in FIG. 1, but is provided with a separate monitor 34, on which the analog ECG from the output 20 signal is displayed.

Figure 3:
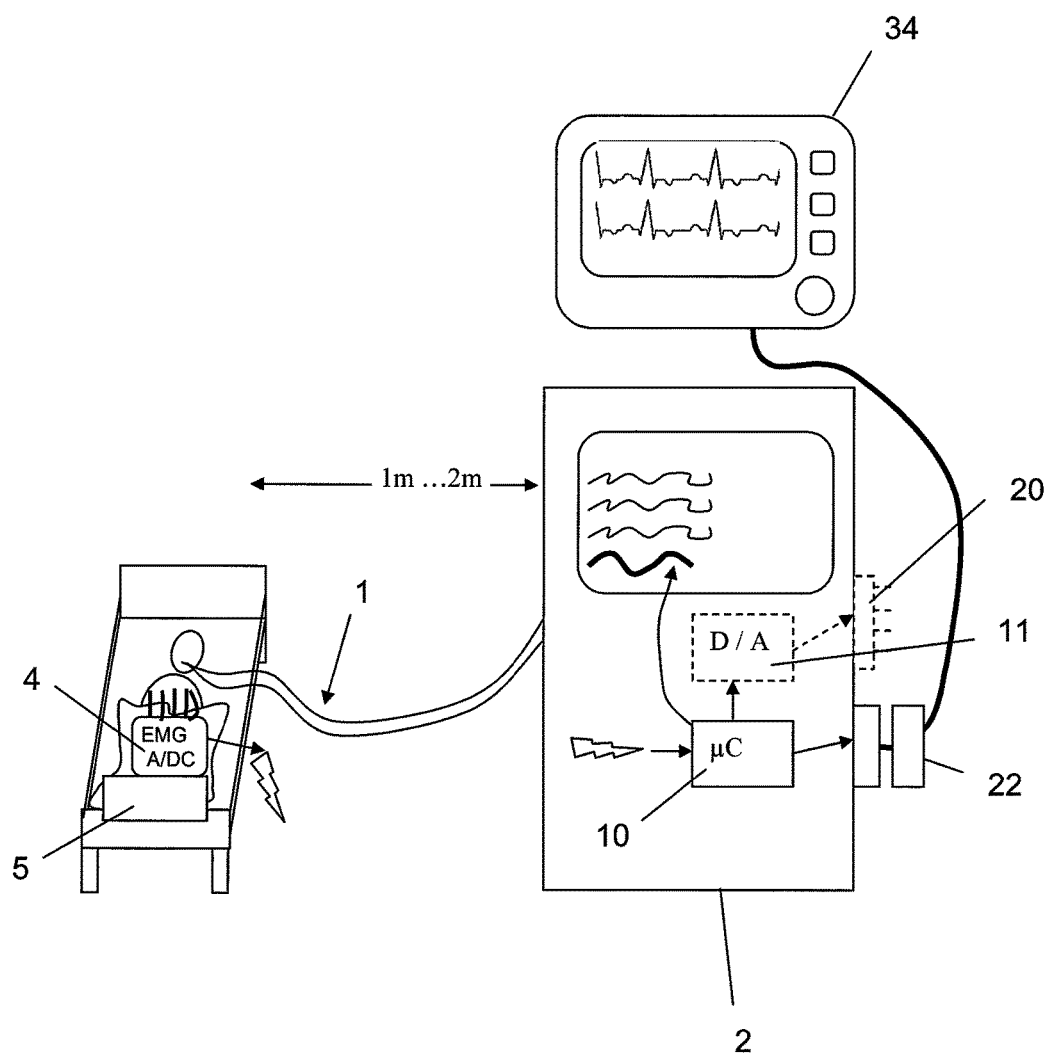
FIG. 3 is a schematic view of a respiration system according to the invention.

FIG. 3 shows another embodiment of a respiration system, which differs from the previous ones by the fact that no electrical line connections are present between the patient module 4 and the main unit 2. The patient module 4 is supplied with electric energy from a local battery 5, instead. The EMG signals picked up and digitized are then transmitted in a wireless manner via radio to the control device 10 in the main unit 2. After separation of the ECG signals, these are made available at the digital output 22 and sent to the monitor 34 and displayed there.

Figure 4A:
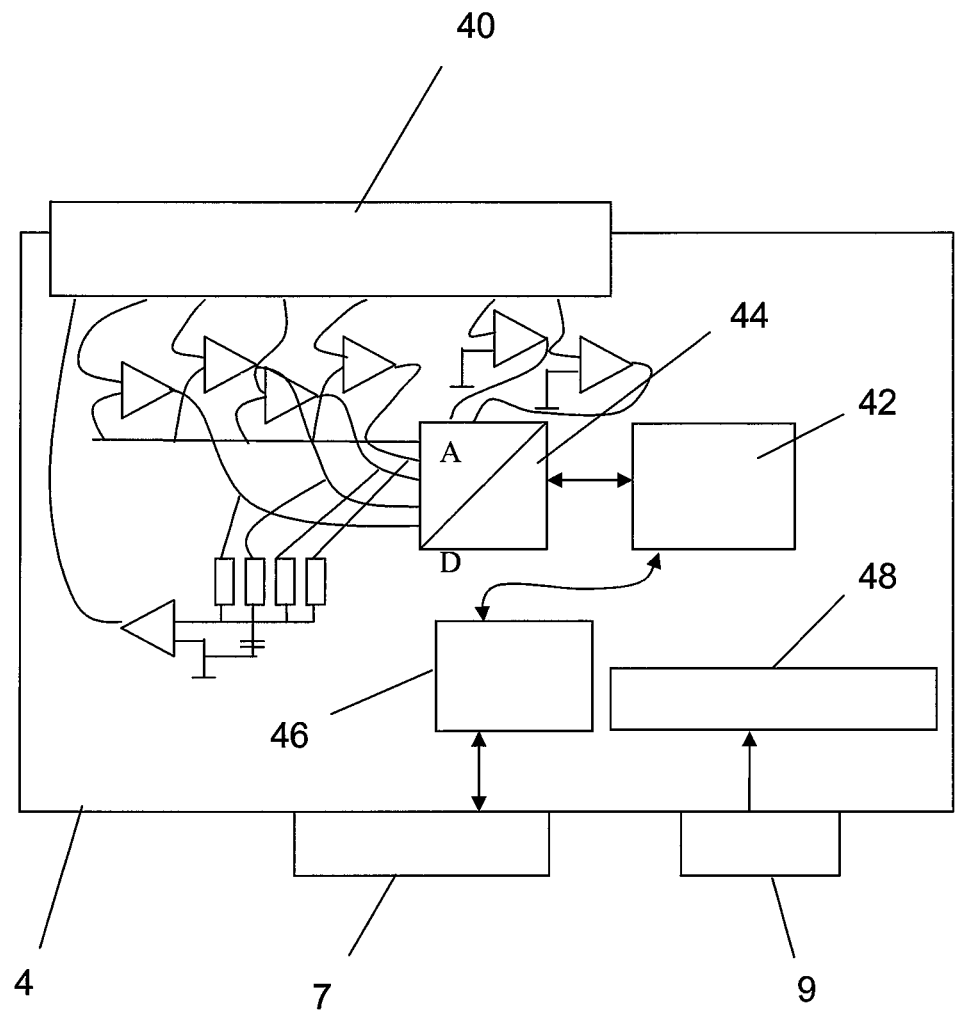
FIG. 4a is a schematic view of a patient module of a respiration system according to the invention.

FIG. 4a schematically shows a patient module 4. The electrode signals are sent via a plug-type connector 40 for the electrodes to measuring amplifiers and the output of these amplifiers is sent to an analog/digital converter 44. The digitized signals are processed in the control device (microprocessor) 42, and, among other things, ECG signals are separated, and they are sent to a line driver 46. The signals thus processed are sent via an output 7 to the main unit. The energy is supplied either via a line 9 or via a local battery. The transmission of the electric energy via the unit 48 to the other components on the patient module 4 is omitted in the diagram for clarity's sake.

Figure 4B:
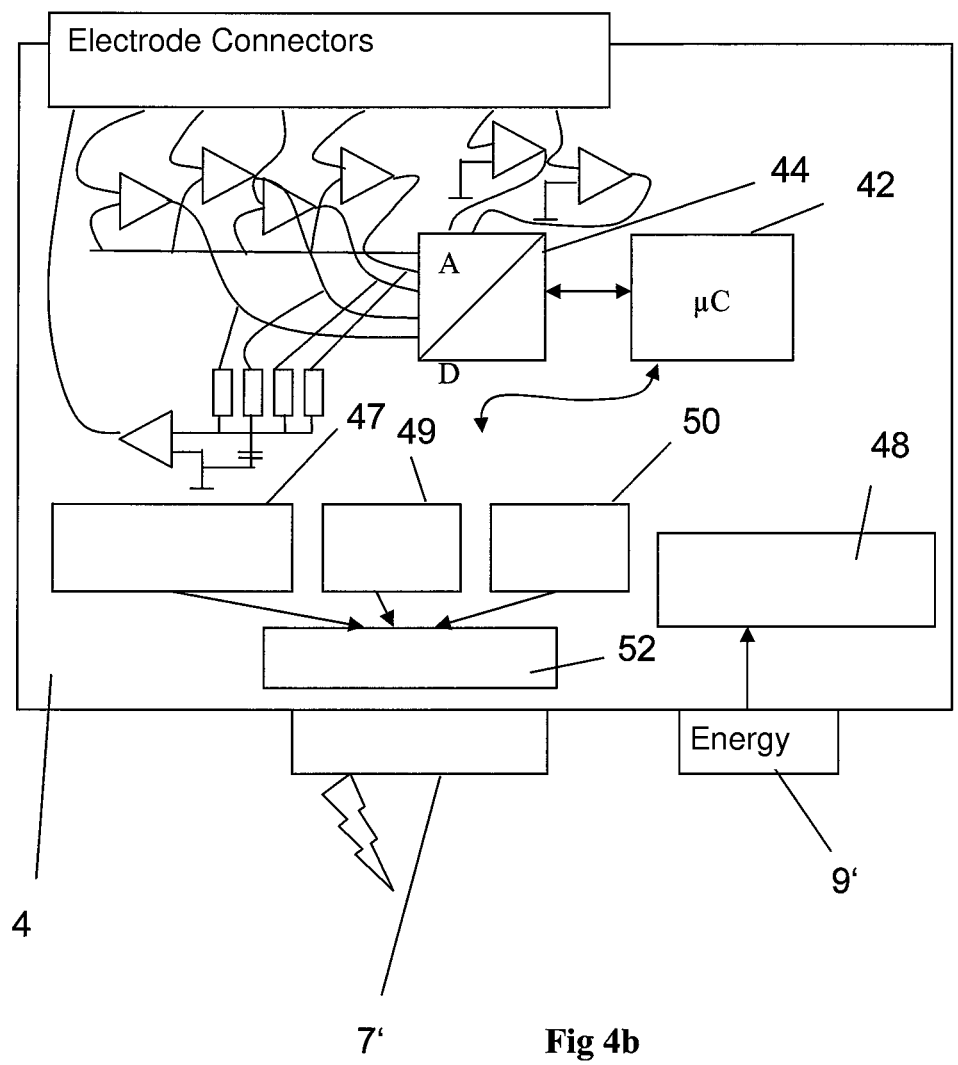
FIG. 4b is a schematic view of a patient module of a respiration system according to the invention.

FIG. 4b shows a modified embodiment of a patient module 4. The electrode signals are again digitized in an analog/digital converter 44 and processed by a control device (control means) 42. After separation of the ECG signals from the electrode signals, an envelope is generated for the surface EMG signals in the control device (microprocessor) 42. The surface EMG signals are sent via the circuits 47 and 49 to a driver 52. The separated ECG signals are correspondingly sent to the driver 52 via a circuit 50. The data are transmitted from the driver 52 via a data transmission unit 7' to the main unit 2 in a wireless manner, for example, via WLAN. The energy is supplied from a battery 9' and a distributor 48, and the lines leading further from the distributor 48 to the individual components on the patient module are likewise omitted for clarity's sake.

While specific embodiments of the invention have been shown and described in detail to illustrate the application of the principles of the invention, it will be understood that the invention may be embodied otherwise without departing from such principles.

APPENDIX

List of Reference Numbers

1 Tube system
2 Main unit
4 Patient module
5 Battery
6 DC-DC converter circuit
7 Data transmission line
7' Data transmission unit
8 Circuit for potential separation
9 Line
9' Battery
10 Control device
20 Analog ECG output
22 Digital ECG output
30 Monitor
32 Display window
34 Screen
40 Plug-type electrode connector
42 Control device
44 A/D converter
46 Line driver
47 Control device for envelope computation
48 Voltage filter
49 Circuit for processing the surface EMG signals
50 Circuit for processing the ECG signal components
52 Line driver

What is claimed is:

1. A respiration system for noninvasive respiration, the respiration system comprising:
   a respirator with a display and a respiration drive;
   a patient module with electrodes for picking up electrode signals from the surface of the chest of a patient, the electrode signals including electrocardiogram (ECG) signals and electromyographic (EMG) signals; and
   a control device controlling the respiration drive, the control device comprising a microprocessor, the control device being configured to receive patient module signals, based on the electrode signals and including the ECG signals and the EMG signals, from the patient module, to suppress the ECG components in the patient module signals in order to obtain the EMG signals representing the breathing effort and to control the respiration drive as a function of the EMG signals, the control device picking up the ECG signals from the patient module signals before the ECG signal component is suppressed and making data representative of the ECG signals, picked up from the patient module signals before the ECG signal component is suppressed, available for display, the control device further being configured to form an envelope for the EMG signals, after separation of the ECG signals, and to display the envelope for the EMG signals on the display of the respirator, to determine a heart rate as a measured value from the ECG signal and to display the heart rate together with the ECG signal on the respirator or to make the heart rate together with the ECG signal available at outputs for separate monitor display; wherein the patient module comprises circuits to separate the ECG signals from the patient module signals and to make the separated ECG signals available for display in the digital and/or analog form.

2. A respiration system in accordance with claim 1, further comprising:
   connection lines wherein the patient module is connected with the respiration drive and the control device by the connection lines, the connection lines supplying energy for the patient module and providing data transmission between the patient module and at least one of the respiration drive and the control device.

3. A respiration system in accordance with claim 1, wherein the patient module is provided with a battery for energy supply and is in radio connection with the respiration drive and the control device in a wireless manner.

4. A respiration system in accordance with claim 1, further comprising a separate monitor for displaying the ECG signals made available at the outputs.

5. A respiration system in accordance with claim 1, wherein a single display is provided for displaying the EMG signals and the ECG signals.

6. A respiration system in accordance with claim 5, wherein the single display provides a window of the display of the ECG signals.

7. A respiration system comprising:
   a respirator with a respiration drive;
   a patient module with electrodes for picking up electrode signals from the surface of the chest of a patient, the patient module providing an output of module electrode signals including electrocardiogram (ECG) signals and electromyographic (EMG) signals formed from the electrode signals; and a control device controlling the respiration drive, the control device comprising a microprocessor, the control device receiving the module electrode signals including electrocardiogram (ECG) signals and electromyographic (EMG) signals, the control device extracting the electrocardiogram (ECG) signals from the module electrode signals and forming data representative of the ECG signals for display and the control device suppressing electrocardiogram (ECG) components in the module electrode signals to obtain the electromyographic signals (EMG signals) representing the breathing effort and the control device controlling the respiration drive as a function of the EMG signals, the control device further forming an envelope for the EMG signals, after separation of the ECG signals, and forming EMG envelope display signals, from the formed envelope for the EMG signals, for display on the respirator, and determining a heart rate as a measured value from the ECG signal and displaying the heart rate together with the ECG signal on the respirator or making the heart rate together with the ECG signal available at outputs for separate monitor display; wherein the control device includes circuits at the patient module to separate the ECG signals from the module electrode signals and to make the separated ECG signals available for display in the digital and/or analog form.

8. A respiration system in accordance with claim 7, further comprising:
connection lines wherein the patient module is connected with the control device by the connection lines, the connection lines supplying energy for the patient module and providing data transmission between the patient module and the control device.

9. A respiration system in accordance with claim 7, wherein the patient module is provided with a battery for supplying energy and is in radio connection with the control device in a wireless manner.

10. A respiration system in accordance with claim 7, further comprising a separate monitor for displaying the ECG signals made available at the outputs.

11. A respiration system in accordance with claim 7, wherein a single display is provided for displaying the EMG signals and the ECG signals.

12. A respiration system comprising:
a respirator comprising a main unit, a respiration drive one or more separate monitor display outputs and a respirator display;
a patient module with electrodes picking up module electrode signals from a surface of a chest of a patient, the module electrode signals including electrocardiogram (ECG) signals and electromyographic (EMG) signals; and a control device controlling the respiration drive, the control device comprising a microprocessor, the control device receiving module electrode signals from the electrodes, the control device separating electrocardiogram (ECG) signals from the module electrode signals and forming data representative of the ECG signals for display on the respirator display and the control device obtaining electromyographic signals (EMG signals), representing the breathing effort, from the module electrode signals by suppressing electrocardiogram (ECG) components in the module electrode signals from the electrodes, wherein the control device forms the data representative of the ECG signals for display from the module electrode signals before the ECG signal component is suppressed and the control device controls the respiration drive as a function of the EMG signals obtained, the control device further forms an envelope for the EMG signals after separation of the ECG signals and displays the envelope for the EMG signals on the respirator display, and determines a heart rate as a measured value from the ECG signal and at least one of:

displays the heart rate together with the ECG signal on the respirator display; and makes available the heart rate together with the ECG signal at the one or more separate monitor display outputs for display of the heart rate together with the ECG signal; wherein the control device includes circuits at the patient module to separate the ECG signals from the module electrode signals and to make the separated ECG signals available for display in the digital and/or analog form.

13. A respiration system in accordance with claim 12, further comprising:
connection lines wherein the patient module is connected with the control device by the connection lines, the connection lines supplying energy for the patient module and providing data transmission between the patient module and the control device.

14. A respiration system in accordance with claim 12, wherein the patient module is provided with a battery for supplying energy and is in radio connection with the control device in a wireless manner.

15. A respiration system in accordance with claim 12, further comprising a separate monitor for displaying the ECG signals.

16. A respiration system in accordance with claim 12, wherein a single display is provided for displaying the EMG signals and the ECG signals.

* * * * *